US010369014B2

(12) United States Patent
Penenberg et al.

(10) Patent No.: US 10,369,014 B2
(45) Date of Patent: *Aug. 6, 2019

(54) METHODS AND INSTRUMENTS FOR USE IN MINIMALLY INVASIVE HIP SURGERY

(71) Applicant: MICROPORT ORTHOPEDICS HOLDINGS INC., Tiel (NL)

(72) Inventors: Brad L. Penenberg, Los Angeles, CA (US); Irina Timmerman, Bartlett, TN (US); Christopher R. McKnett, Cordova, TN (US)

( * ) Notice: Subject to any disclaimer, the term of this patent is extended or adjusted under 35 U.S.C. 154(b) by 69 days.

This patent is subject to a terminal disclaimer.

(21) Appl. No.: 15/401,193

(22) Filed: Jan. 9, 2017

(65) Prior Publication Data

US 2017/0128233 A1 May 11, 2017

Related U.S. Application Data

(63) Continuation of application No. 14/936,468, filed on Nov. 9, 2015, now Pat. No. 9,539,113.

(51) Int. Cl.
*A61F 2/46* (2006.01)
*A61B 17/00* (2006.01)
(Continued)

(52) U.S. Cl.
CPC ...... *A61F 2/4609* (2013.01); *A61B 17/00234* (2013.01); *A61B 17/1746* (2013.01); *A61B 17/92* (2013.01); *A61B 17/1666* (2013.01); *A61F 2/34* (2013.01); *A61F 2002/3054* (2013.01); *A61F 2002/30233* (2013.01); *A61F 2002/30364* (2013.01); *A61F 2002/30377* (2013.01); *A61F 2002/30487* (2013.01);
(Continued)

(58) Field of Classification Search
CPC .... A61F 2/4609; A61B 17/1746; A61B 17/92
See application file for complete search history.

(56) References Cited

U.S. PATENT DOCUMENTS 4,475,549 A 10/1984 Oh
6,676,706 B1 1/2004 Mears
(Continued)

FOREIGN PATENT DOCUMENTS

CA 2343926 A1 10/2001
EP 1149562 A2 10/2002
(Continued)

OTHER PUBLICATIONS

Berry, et al., Symposium on Minimally Invasive THA, J. Bone Joint Surg. 85A:2235-2246 (2003).
(Continued)

*Primary Examiner* — Ellen C Hammond
(74) *Attorney, Agent, or Firm* — Walk Cook Lakey PLC

(57) ABSTRACT

A method of providing a minimally invasive hip arthroplasty in conjunction with a main incision formed through a patient's skin and soft tissue in the patient's hip, including providing an instrument having a main body and an arrangement for guiding the formation of a portal incision and a small path to the patient's acetabulum along an impaction axis. A trocar is placed through a guide ring on an arm of the instrument to form the portal incision and small path. Impaction of an acetabular shell is carried out along the impaction axis thus formed.

11 Claims, 12 Drawing Sheets

(51) Int. Cl.
*A61B 17/17* (2006.01)
*A61B 17/92* (2006.01)
*A61F 2/34* (2006.01)
*A61F 2/30* (2006.01)
*A61B 17/16* (2006.01)

(52) U.S. Cl.
CPC ............... *A61F 2002/30617* (2013.01); *A61F 2002/30787* (2013.01); *A61F 2002/3401* (2013.01); *A61F 2002/3404* (2013.01); *A61F 2002/4629* (2013.01); *A61F 2002/4635* (2013.01); *A61F 2002/4681* (2013.01); *A61F 2220/0025* (2013.01); *A61F 2220/0033* (2013.01); *A61F 2230/0069* (2013.01); *A61F 2250/0097* (2013.01)

(56) References Cited

U.S. PATENT DOCUMENTS

| | | |
|---|---|---|
| 6,695,850 B2 | 2/2004 | Diaz |
| 6,905,502 B2 | 6/2005 | Penenberg |
| 6,997,928 B1 | 2/2006 | Penenberg |
| 7,833,229 B2 | 11/2010 | Penenberg |
| 8,740,907 B2 | 6/2014 | Penenberg |
| 2002/0099447 A1 | 7/2002 | Mears et al. |
| 2002/0116067 A1 | 8/2002 | Mears et al. |
| 2003/0158559 A1 | 8/2003 | Diaz |
| 2003/0220696 A1 | 11/2003 | Mears et al. |
| 2003/0229352 A1 | 12/2003 | Penenberg |

FOREIGN PATENT DOCUMENTS

| | | |
|---|---|---|
| EP | 1149562 A3 | 1/2003 |
| WO | 03/065906 A2 | 8/2003 |

OTHER PUBLICATIONS

Pelligrini et al. Surgical Approaches to th Hip Joint. Surgery of the Musculoskeletal System (C. M. Evarts, Ed.), Churchill Livingstone (New York, NY); Chapter 94, pp. 2734-2756 (1990).

Innomed MIS catalog (2003).

Light, TR; Keggi, KJ. Anterior Approach to Hip Arthroplasty, Clin. Orthop. Rel. Res. 152:255-260 (1980).

McTighe, T. A New Era of Minimally Invasive Surgical Approaches for THA, JISRF Update (Dec. 2002), pp. 1-8.

Kennon, RE et al. Total Hip Arthroplasty Through a Minimally Invasive Anterior Surgical Approach. J. Bone Joint Surg. Am. 85:39-48 (2003).

Keggi, KJ, et al. Anterior Approach to Total Hip Replacement: Surgical Technique and Clinical Results of Our First One . . . Yale J. Biol. Med. 66:243-256 (1993).

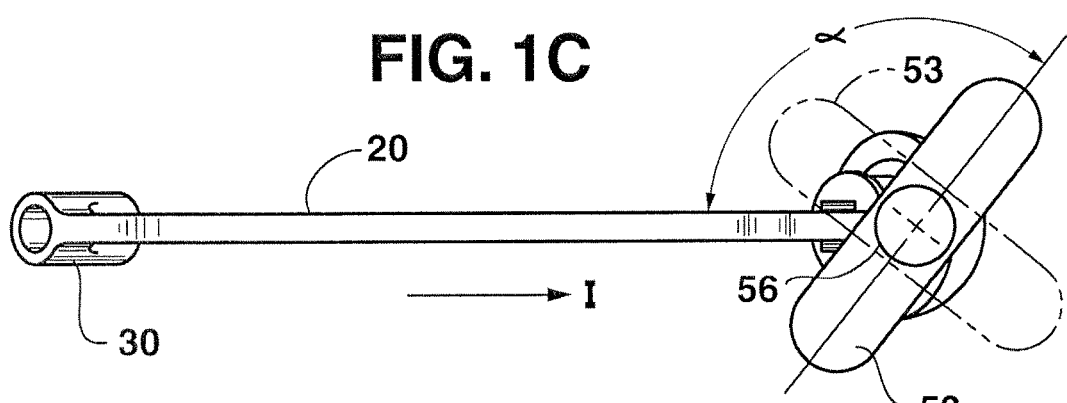
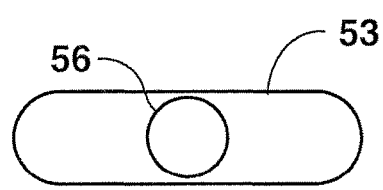
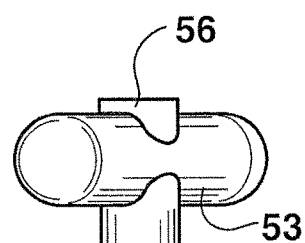
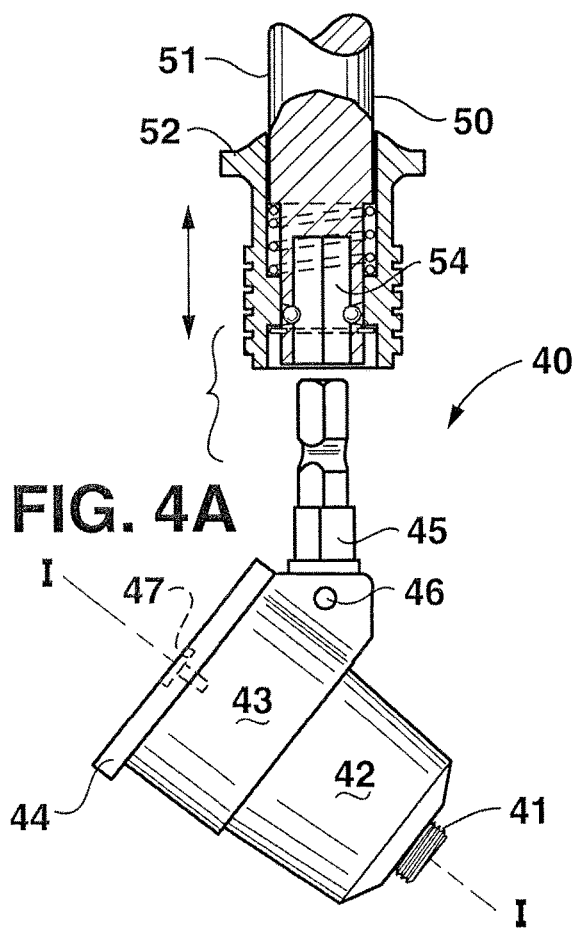
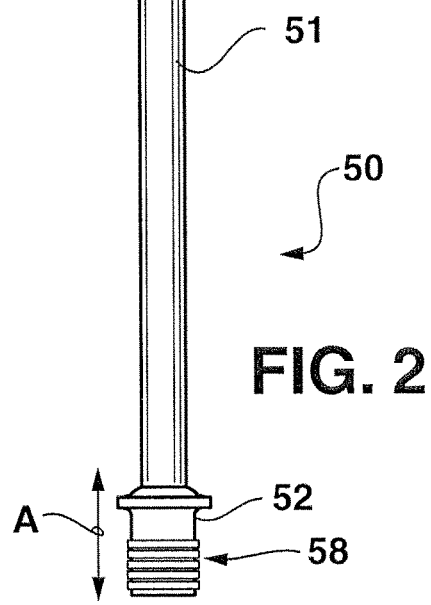

METHODS AND INSTRUMENTS FOR USE IN MINIMALLY INVASIVE HIP SURGERY

CROSS REFERENCE TO RELATED APPLICATIONS

This application is a continuation of, claims priority to, and incorporates by reference application Ser. No. 14/936,468 filed Nov. 9, 2015, now U.S. Pat. No. 9,539,113; application Ser. No. 13/791,001 filed Mar. 8, 2013, now U.S. Pat. No. 9,180,023; application Ser. No. 12/692,294, filed Jan. 22, 2010, now U.S. Pat. No. 8,439,928; and application Ser. No. 10/794,220, filed Mar. 5, 2004, now U.S. Pat. No. 7,651,501. This patent application is related to co-pending U.S. patent application Ser. No. 10/166,209, filed Jun. 10, 2002, published as U.S. Patent Application Publication 2003/0229352A1, entitled, "Apparatus for, and Method of, Providing a Hip Replacement."

FIELD OF THE INVENTION

This invention is generally directed to an instrument for use in minimally invasive (MIS) hip surgery. The invention is more specifically directed to an instrument useful in the various steps related to the implantation of an acetabular prosthesis via MIS methods.

BACKGROUND OF THE INVENTION

Traditionally, hip replacement surgery has been done via "open" surgical procedures. With open procedures, space for inserting and manipulating surgical instruments is not that critical and it is easier to get around major anatomical features, such as the greater trochanter of the femur.

However, with the advent of minimally-invasive surgical procedures for hip replacement, small incision sizes combined with tight anatomical clearances have resulted in the need for surgical instruments that take maximum advantage of available space.

All patents and publications mentioned herein are incorporated by reference herein.

While these devices may be acceptable for their intended or described uses, they are often complex and not geometrically and spatially optimized.

Accordingly, there is room for improvement within the art.

OBJECTS AND SUMMARY OF THE INVENTION

It is an object of the invention to provide an instrument for use in minimally invasive hip surgery.

It is a further object of the invention to provide a method of using the instrument.

These and other objects of the invention are achieved by An instrument for use in hip arthroplasty, comprising: a main body; an impaction body attached to an end of the main body and positionable inside the hip of a patient, the impaction body having an axis coaxial with an impaction axis; an arm extending from the main body and having a guide ring at an end thereof, the guide ring having an axis coaxial with an impaction axis; a removable trocar; and a removable impacting instrument.

These and other objects of the invention are achieved by an instrument for use in hip arthroplasty, comprising: a main body, the main body having a rotatable handle; an impaction body attached to an end of the main body and positionable inside the hip of a patient, the impaction body having an axis coaxial with an impaction axis; wherein the position of the handle indicates that the main body is in the proper position.

These and other objects of the invention are achieved by an instrument for the impaction of an acetabular shell, comprising: an impaction body, the impaction body having a threaded stud at a first end thereof and a rim connected to the threaded stud at its other end such that the position of the acetabular shell can be varied without loosening the shell from the stud.

BRIEF DESCRIPTION OF THE DRAWINGS

FIG. 1C is a top view of an exemplary embodiment of an instrument according to the invention.

FIG. 2 is a top view of the main body of the instrument according to the invention.

FIG. 3 is an elevation view of the main body of the instrument according to the invention.

FIG. 4A is an elevation view of the impaction portion of the instrument according to the invention.

PREFERRED EMBODIMENTS OF THE INVENTION

With respect to the above-referenced figures, an exemplary embodiment of a an instrument and method of using the instrument that meets and achieves the various objects of the invention set forth above will now be described.

Figure 1A:
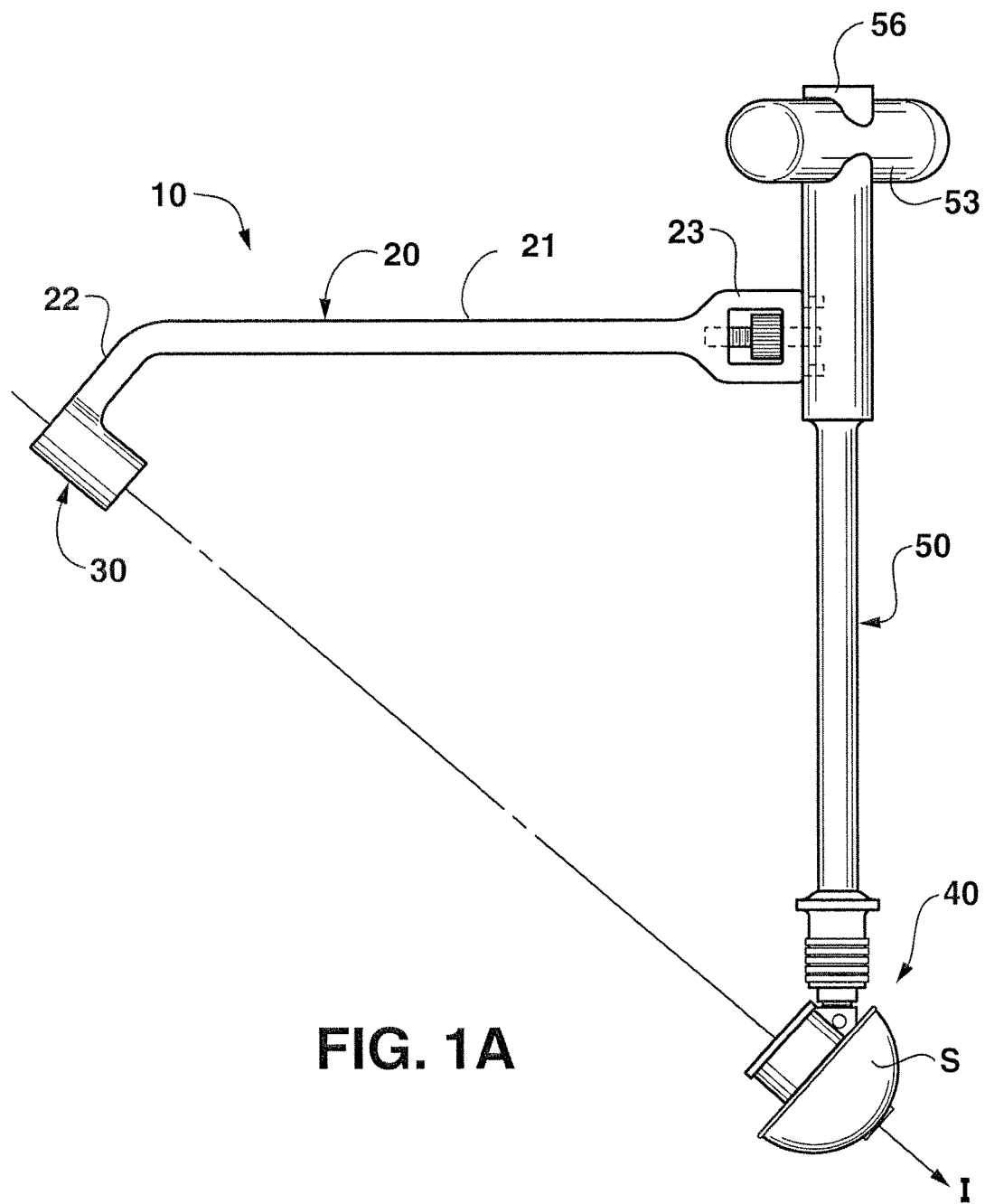
FIG. 1A is an elevation view of an exemplary embodiment of an instrument according to the invention.
Figure 1B:
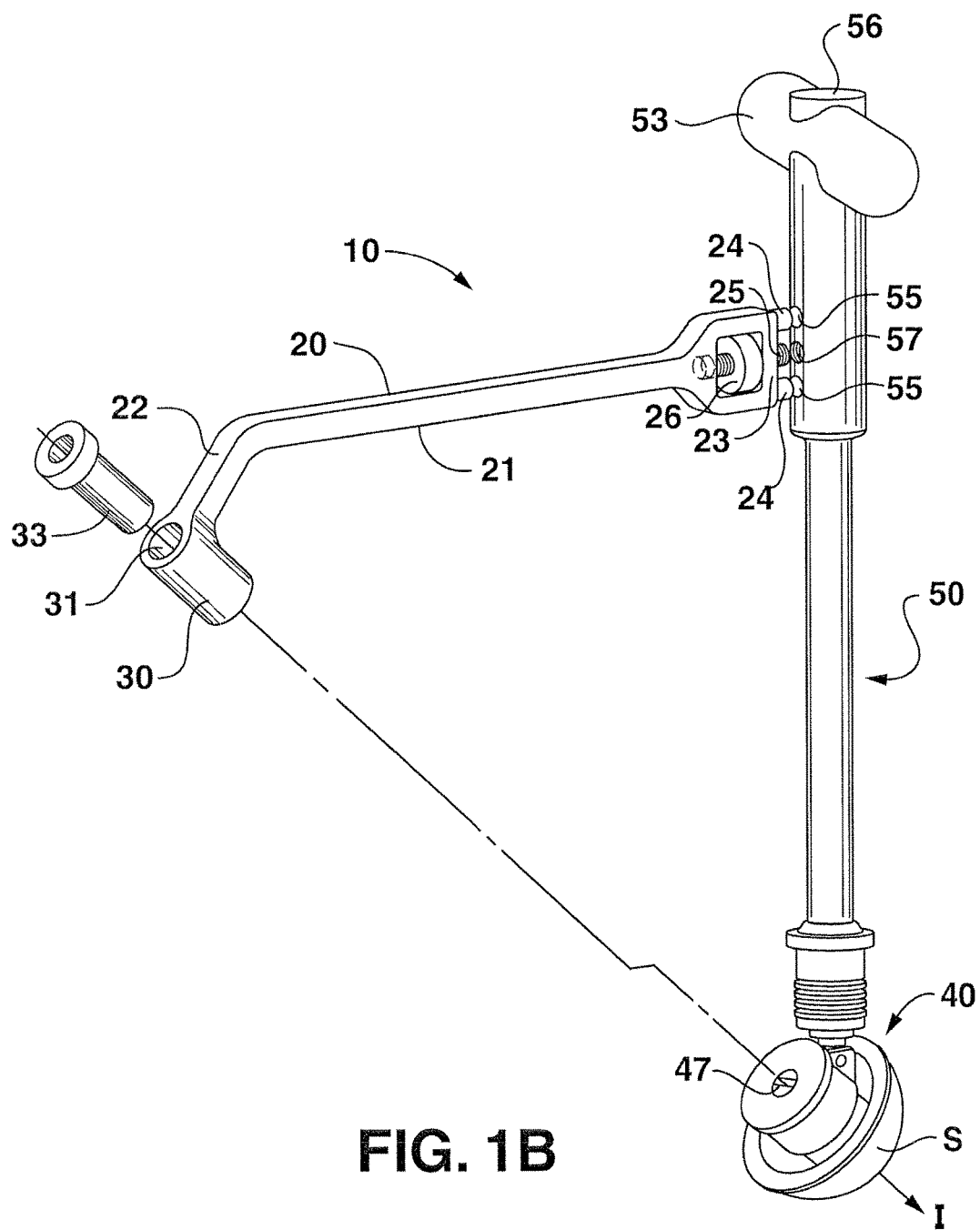
FIG. 1B is a perspective view of an exemplary embodiment of an instrument according to the invention.

FIG. 1A is an elevation view, FIG. 1B is a perspective view, and FIG. 1C is a top (plan) view of an exemplary embodiment of the instrument 10 according to the invention. The instrument 10 is preferably modular, comprising three separable main parts, namely: main body 50, arm 20, and impaction body 40.

Arm 20 may comprise two portions, namely a extended first arm portion 21 (extending outwardly away from main body 50) and a downwardly angled second arm portion 22. At an end of second arm portion 22 is a guide ring 30, including a guide bore 31. It is possible to omit downwardly angled second arm portion 22 and lower and/or lengthen extended first arm portion 21. However, then the angle between guide ring 30 and first portion 21 would be sharper.

Furthermore, it is possible for arm 20 to be a single curved arm. The structure shown herein is merely an exemplary embodiment.

At the other end of first arm portion 21, a releasable connection 23 is provided so that the arm 20 may be selectively attached and detached from main body 50. While the details of releasable connection 23 are not critical to the invention, one form of releasable connection 23 may be that shown in the drawings. Pins 24 in the end of extended arm portion 21 are to be received within bores 55 of main body 50 for a guidance function. A rotatable threaded member 25 is received in a threaded bore 57 of main body 50 to provide the securing function. Threaded member 25 may include a thumb wheel 26 for ease of operation.

As shown in FIGS. 1A and 1B, the longitudinal axis of guide bore 31 is coincident and coaxial with a keyed bore 47 (whose function is further described below) in impaction body 40, which itself is coincident and coaxial with the center of acetabular shell S and the proper impaction direction/axis I for acetabular shell S. As used herein, the impaction axis/direction I means the direction in which the axis of rotation of the acetabular shell S is properly aligned and typically coaxial with the main axis of the patient's acetabulum A or perpendicular to the plane of the opening of the acetabular shell S. Impaction in this direction is important to minimize rotation of the acetabular shell S during final seating.

FIG. 2 is an elevation view of main body 50. Main body 50 generally comprises an elongated body 51. At a first end of elongated body 51 is a handle 53, which typically will be transverse to elongated body 51. At the opposite end of elongated body 51 from handle 53 is a locking unit 55. The details of locking unit 55 may vary and are typically conventional, but as an example, locking unit 55 may be actuated by locking sleeve 52, which can slide along the outer surface of elongated body 51 in the direction of the arrows against the bias of springs (not shown). A bore 54 is contained within elongated body 51 for receipt of a conventional locking member 45 of the impaction body 40 (FIG. 4A). Accordingly, through use of locking sleeve 52, locking member 45 can be locked within and released from inside bore 54 of elongated body 51. This makes main body 50 and impaction body 40 selectively separable from each other.

Figure 5:
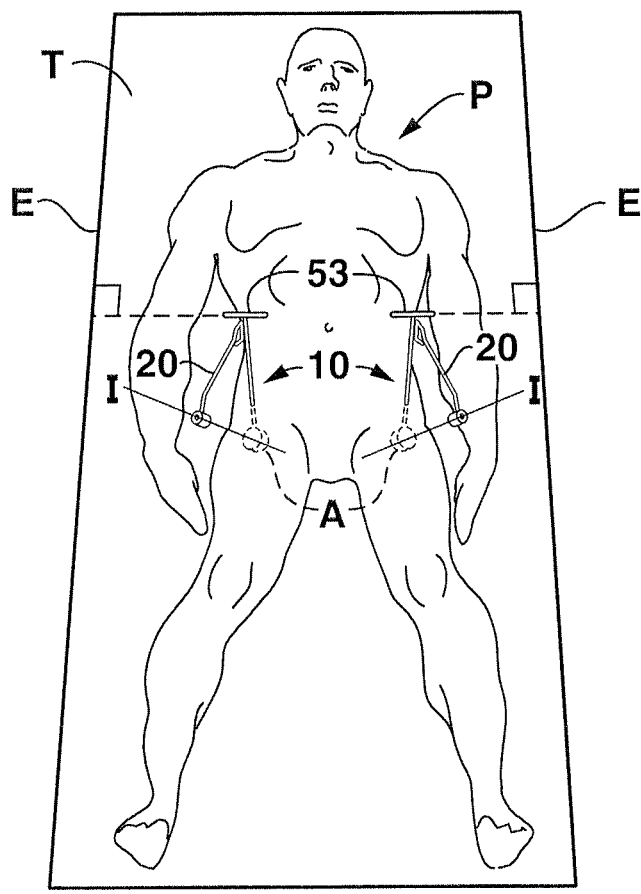
FIG. 5 is a simplified representation of how the instrument according to the invention assures the proper impaction axes.
Figure 6:
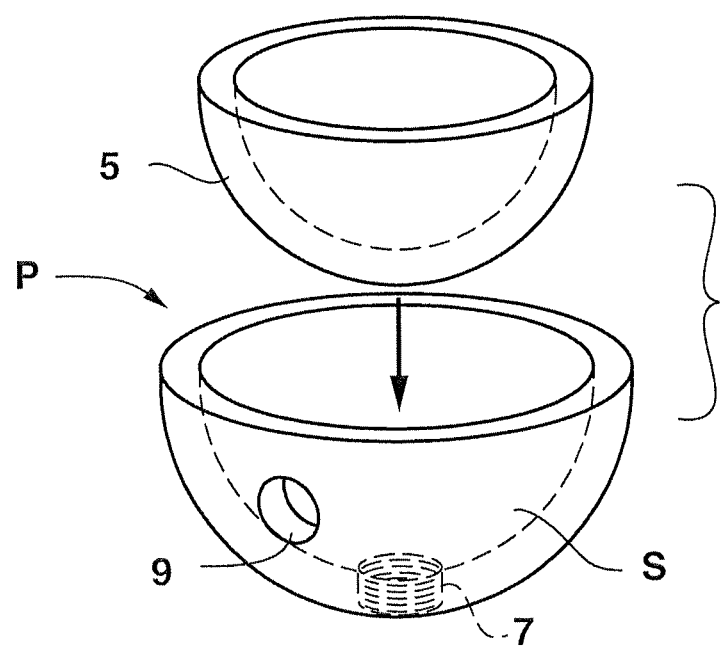
FIG. 6 is a perspective view of an acetabular shell and liner for use with the instrument and method according to the invention.

As shown in FIG. 1C, handle 53 makes a specific angle with respect to arm 20. This angle is such that when instrument 10 is properly used, handle 53 gives the doctor a visual indication that the acetabular shell S is being inserted with the proper version along impaction axis I. This is schematically shown in FIG. 5. FIG. 5 is a schematic plan view depicting the instrument 10 with respect to a patient P having left and right acetabulums A and an operating room table T having long edges E. As shown in FIG. 5, when handle 53 is perpendicular to the long edge of the operating room table T, the impaction axis I is properly aligned with the patient's pelvis and acetabulums A regardless of whether a left or right hip is being operated on. While the patient P is shown in the supine position, the instrument may be used with the patient in any position including supine or lateral.

To allow the instrument to be used for both left and right hips, handle 53 should be adjustable so it may be aligned perpendicular with either long edge E of operating room table T when the instrument is inserted with the proper anteversion. This can be done by the following exemplary non-limiting method. Tightening member 56, which compresses handle 53 against elongated body 51 to prevent movement of handle 53, can be loosened. The position of handle 53 adjusted and then tightening member 56 re-tightened. This allows handle 53 to be aligned with the long edge of the operating room table regardless of whether instrument 10 is going to be used for a left or right hip. Typically, the amount of rotation allowed is 90 degrees. Rotation may be limited by any known means.

Figure 4B:
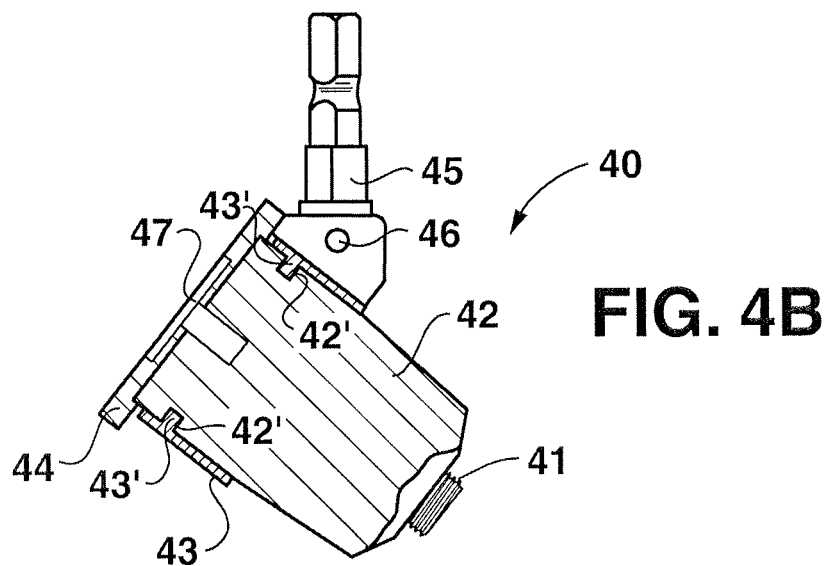
FIG. 4B is a cross-section of the impaction portion of the instrument according to the invention.

FIG. 4A depicts an elevation view of impaction body 40 and FIG. 4B depicts a cross-section of impaction body 40. Impaction body 40 is a modular element that will come in various sizes. The size used typically will be selected based upon the size of the acetabular shell S being impacted. Each size of impaction body 40 will have a conventional locking member 45 so that the impaction body 40 can be separated from or locked to main body 50, as described above.

Opposite the free end of locking member 45 is a mounting element 46, for example, a mounting pin. Mounting element 46 connects locking member 45 to first impaction body portion 43. First impaction body portion 43 is a cylindrical shell and although typically made from steel, may be made from any material capable of being impacted.

Second impaction body portion 42 is also cylindrical, but in this case typically solid and made from a plastic material capable of withstanding impaction. Plastics are preferred so that the edges of second impaction body portion 42 do not scratch or otherwise damage an inner surface of acetabular shell S. Such scratches or damage would typically render an acetabular shell S unusable.

Second impaction body portion 42 can rotate within the shell defined by first impaction body portion 42. Second impaction body portion 42 may have grooves 42' therein for interacting with tongues 43' on the inner walls of first impaction body portion 43 to prevent the separation of the two elements, while still allowing relative rotation. However, any interlocking members may be used which prevent separation of the two elements, while still allowing control of relative rotation.

A threaded stud 41 is mounted on the free end of second impaction body portion 42. Threaded stud 41 is for receiving the acetabular shell S thereon via the conventional threaded hole 7 of the acetabular shell S (FIG. 5). Threaded stud 41 may be mounted on second impaction body portion 42 in any way, such as but not limited to, being spot welded or even unitarily formed therewith.

Rim portion 44 is affixed to the opposite end of second impaction body 42 from threaded stud 41. Accordingly, a doctor may rotate rim portion 44 and cause a resulting rotation in second impaction body 42 and threaded stud 41, for reasons to be discussed below. Rim portion 44 has a keyed bore 47 at the center thereof for receipt of an instrument or tool therein, as will also be described.

As shown in FIG. 4A, the impaction axis I passes through bore 47 and the centers of first and second impaction bodies 43, 42 and threaded stud 41. This allows, as will be described later, the various instruments that are used with instrument I to be smoothly entered and passed through soft tissue, avoiding any hard bone.

As mentioned above, by rotating rim portion 44, this results in rotation of second impaction body 42 and threaded stud 41. This is an important aspect of the invention for the following reason.

FIG. 5 depicts a typical acetabular prosthesis P contemplated for use with the invention. An acetabular shell S is the portion of the prosthesis P that is directly implanted in the natural acetabulum of the patient undergoing hip replacement surgery. Acetabular shell S has a threaded hole 7 at its bottom for attachment to an impacting device such as shown in the invention. After the shell S is implanted, a shell liner 5, most typically made from either: metal, ceramic, or polyethylene (e.g. UHMWPE), is then inserted into the acetabular shell S, in an impacting direction, as shown by the arrow. For situations in which additional fixation between the acetabular shell S and the patient's natural acetabulum is required, screws (not shown), may be passed through one or more screw holes 9 in shell S and into the bone surrounding the acetabulum. The patient's acetabulum would now be ready for receipt of the femoral portion, i.e., femoral head, of the implant. Typically these screws can be affixed in only certain locations in the patient's acetabulum due to bone quality issues. Therefore, there needs to be the ability to align screw holes 9 with those portions of the patient's acetabulum that have good bone. In some prior art devices, once the acetabular shell S was fully screwed onto the threaded stud, there was no ability to fine tune the alignment of screw holes 9 with respect to the acetabulum without loosening the shell S (e.g., rotating it back on the threads). See e.g. U.S. Pat. No. 5,474,560. This could cause problems during impacting or damage the instrument 10 or acetabular shell S. In other prior art devices, the use of flexible cable actuators introduce slack into the drive mechanism that do not allow for the easy and precise fine tuning that is required in surgical applications. See e.g. U.S. Pub 2003/0050645 and WO03/065906. This is especially true when the acetabular shell S is not constrained within the patient's acetabulum. However, with the invention, even with the acetabular shell S completely threaded on threaded stud 41, the position of screw hole 9 with respect to the patient's acetabulum can be fine tuned by rotating rim portion 44.

Figure 7:
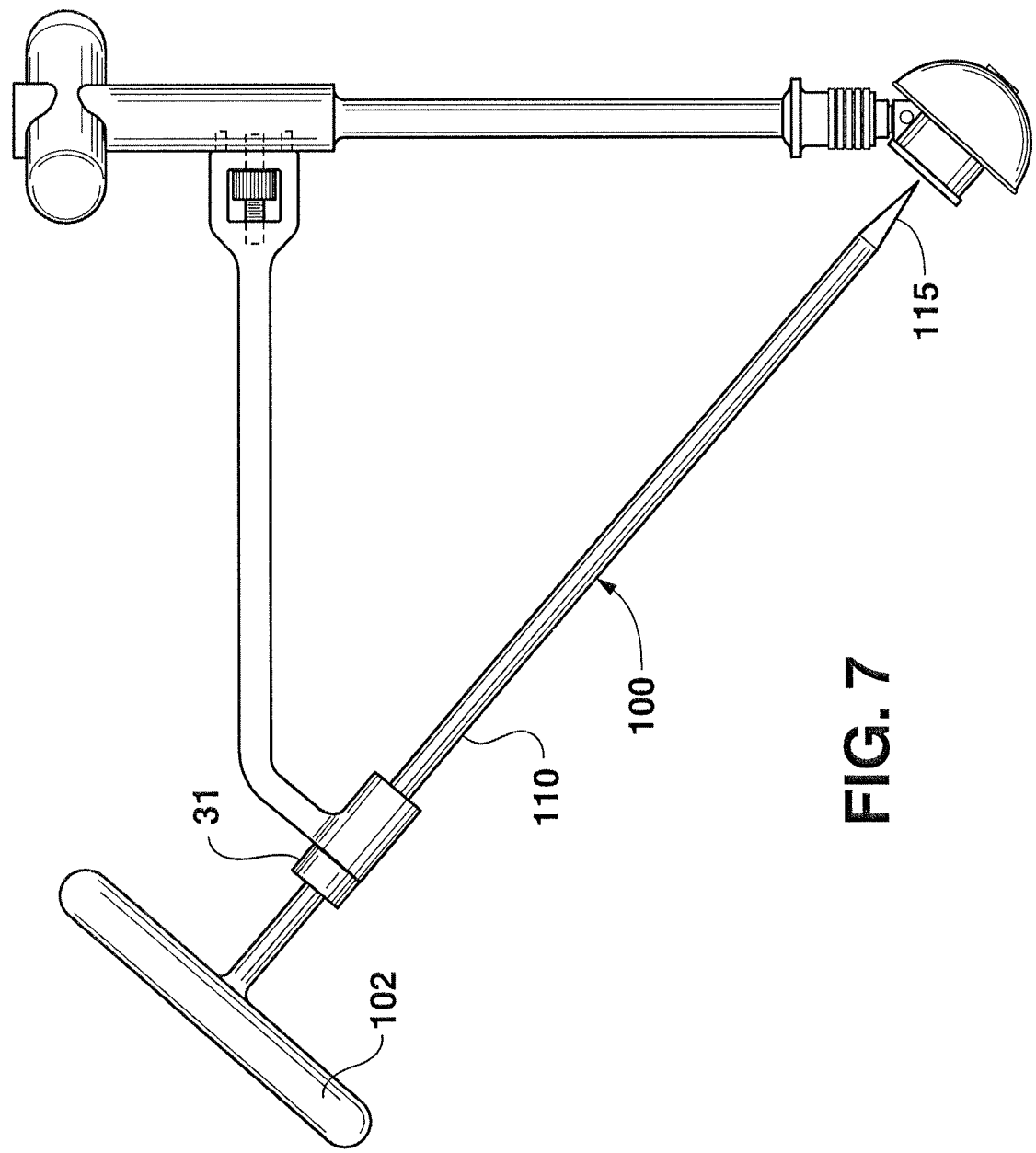
FIG. 7 is an elevation view of a first configuration of the instrument according to the invention.

A first configuration of the instrument 10 according to the invention is shown in FIG. 7. In this configuration, a trocar 100 for piercing the patient's skin is inserted through the guide bore 31 in guide ring 30. Because the shaft 110 of trocar 100 will typically have a smaller diameter than the guide bore 31, a guide sleeve 33 is slipped into the guide bore 31.

Figure 8:
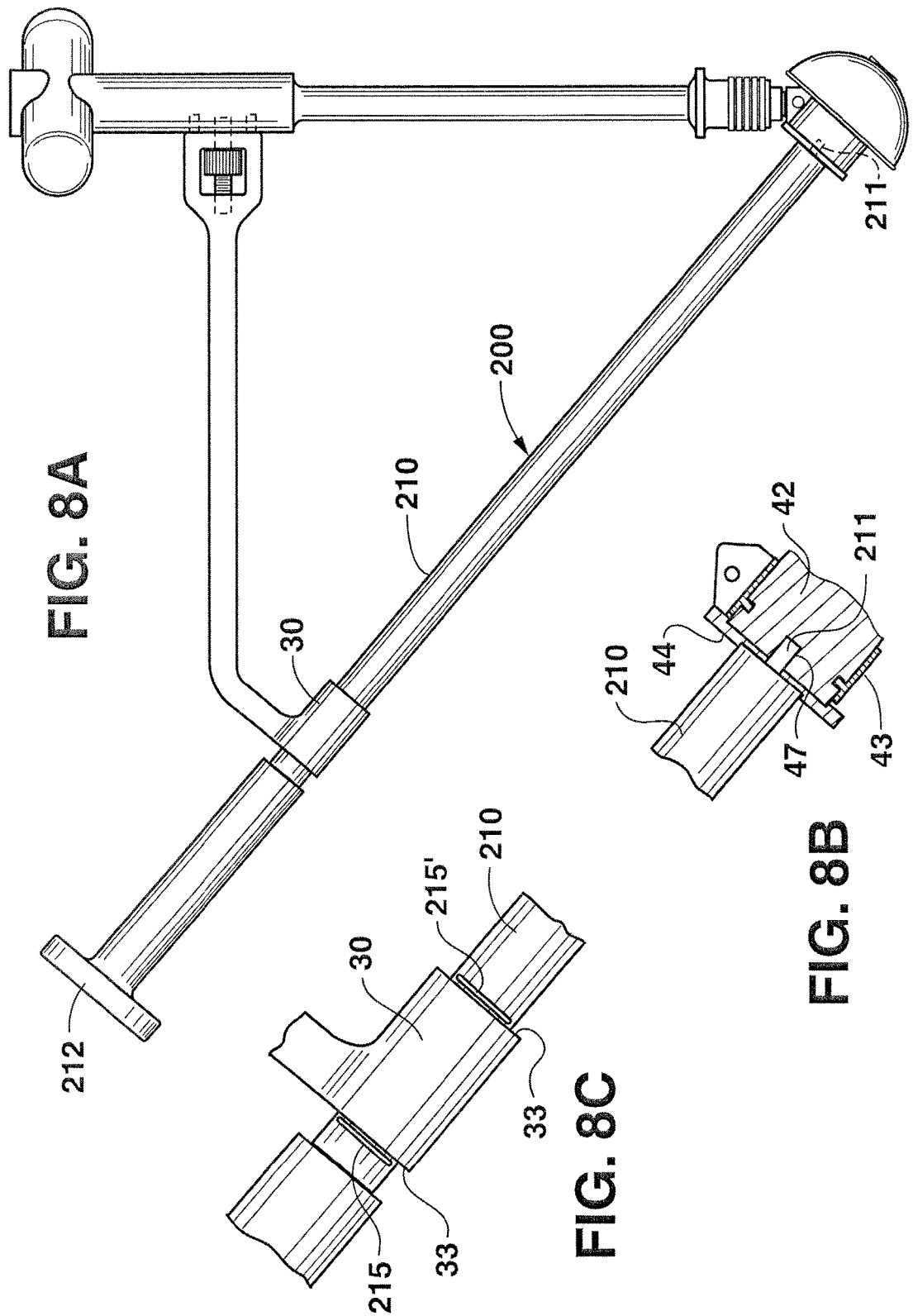
FIG. 8A is an elevation view of a second configuration of the instrument according to the invention.
FIGS. 8B and 8C are cross section and detail views, respectively, of the second configuration of the instrument, as shown in FIG. 8.

The second configuration of the instrument according to the invention is shown in FIG. 8A. In this configuration, the guide sleeve 33 is removed from the guide bore 31 and an impacting instrument 200 is inserted through the guide bore 31 in the guide ring 30 and the keyed bore 47 in rim portion 44. Impacting instrument has an impaction body, which includes an impaction surface 212. At its opposite end, impacting instrument 200 will comprise a keyed tip 211 that matches the keyed bore 47 of rim portion 44 such that when impaction tool 200 is rotated, rotation will be imparted on rim portion 44 (FIG. 8B). Furthermore, shaft 210 of impacting instrument 200 may include laser or other etching 215 (FIG. 8C) that lines up with edges 33 of guide ring 30, so as to indicate that impacting instrument 200 is fully or properly seated within bore 47 of rim 44.

Having described the structure of instrument 10 and its various configurations, its method of use will now be described.

Figure 9:
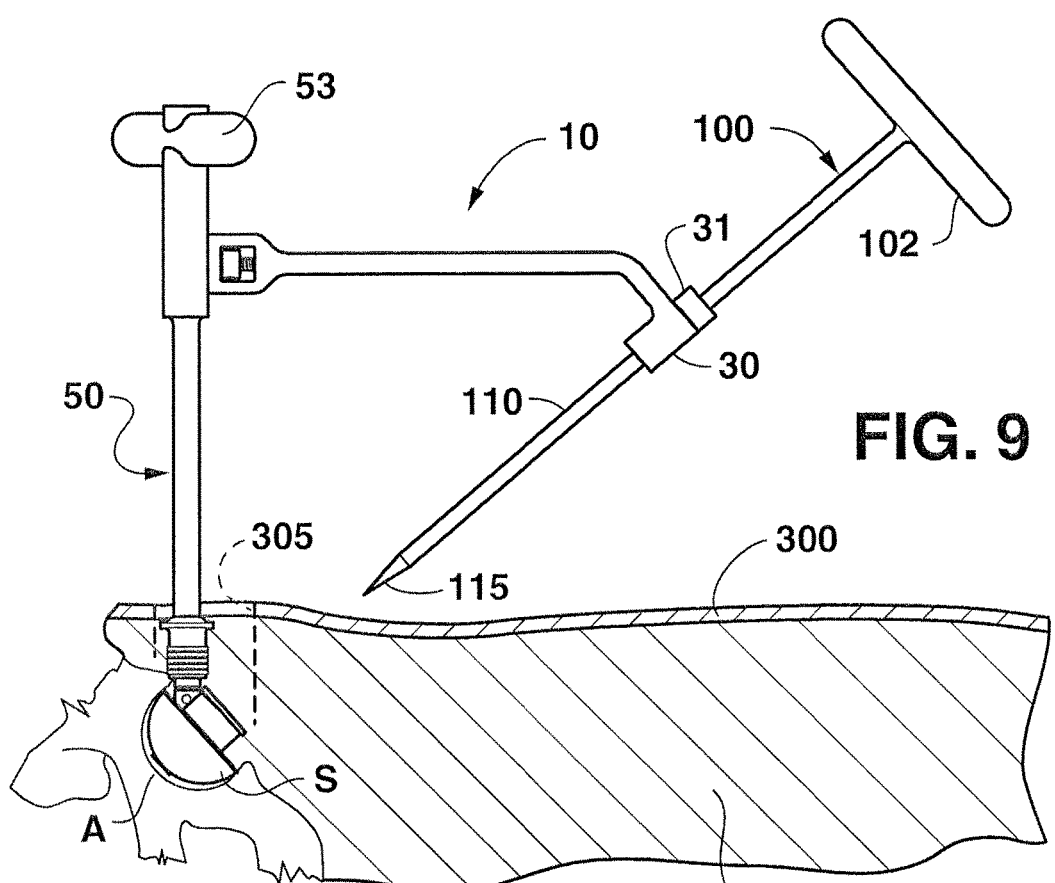
FIGS. 9, 10, 11, 12, 13, and 14 depict various steps in a method of using the instrument according to the invention.

FIG. 9 shows the first stage of the use of instrument 10 during a MIS hip arthroplasty. During this surgery, a main incision 305 has been made which provides primary access to the patient's acetabulum. The details of this main incision can be found in related application US Pub 2003/0229352, whose contents are incorporated by reference herein.

An acetabular shell S is mounted on threaded stud 41 and handle 53 positioned for left or right as previously described, depending upon the hip being operated upon. Main body 50 is inserted into the incision 305 in the patient's skin 300 and acetabular shell S preliminarily aligned with the patient's acetabulum A. If screws are going to be used with acetabular shell S, rim 44 may be rotated until screw holes 9 are lined up with bone suitable for screws. Furthermore, when main body 50 points straight at the ceiling the abduction is correct and when handle 53 is perpendicular to the edge of the operating table, the impaction axis I and version are now correct. Guide sleeve 33 is inserted into guide bore 31 of guide ring 30.

Figure 10:
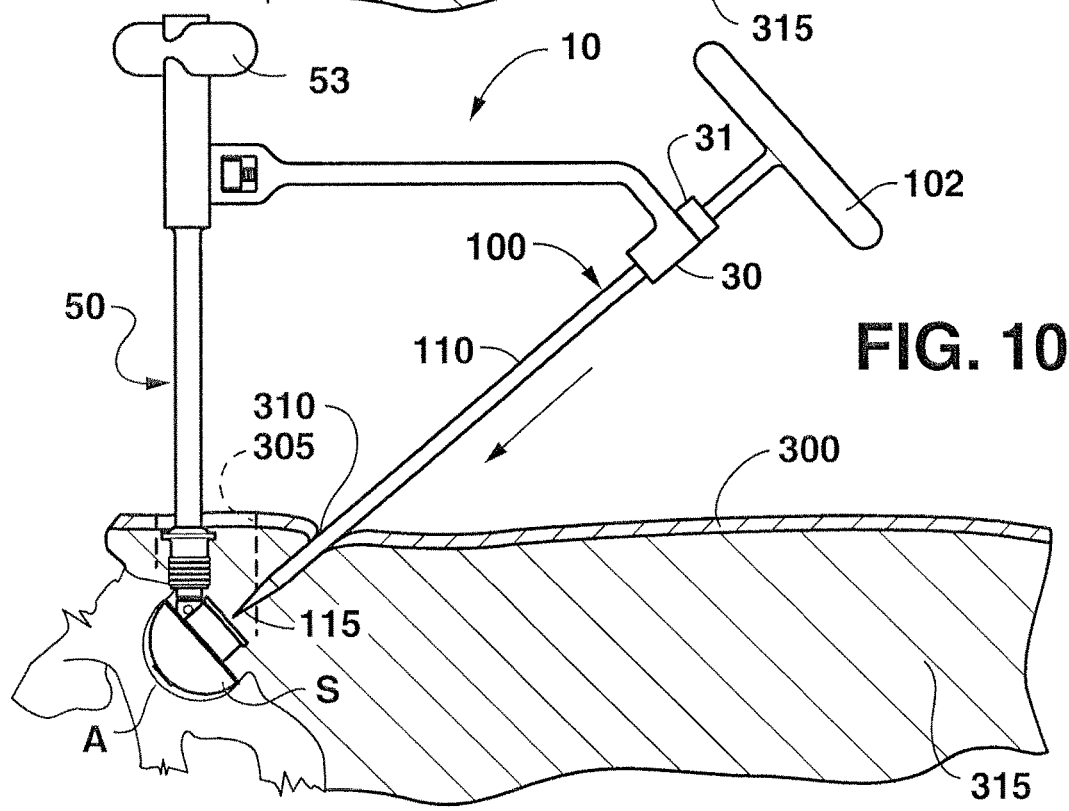
Figure 11:
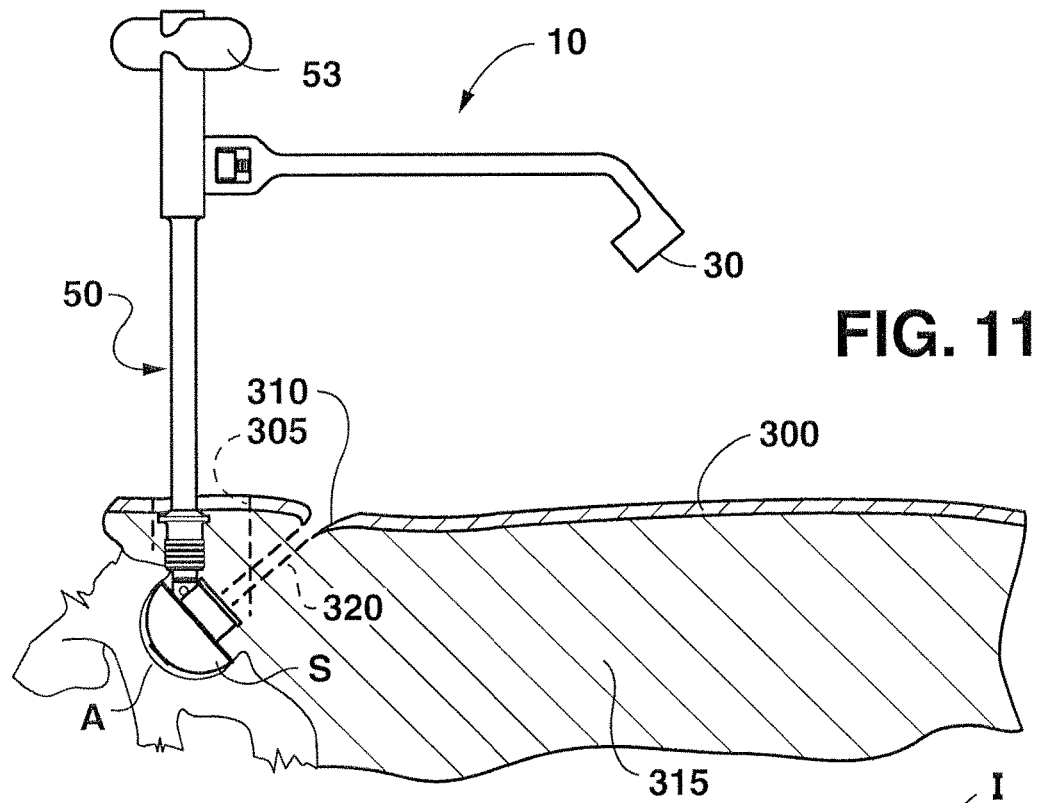

Trocar 100 is inserted through guide sleeve 33 and the doctor manipulates handle 102 until pointed tip 115 approaches the patient's skin 300 and then punctures the skin 300. The doctor continues to push the trocar 100 through the soft tissue 315 until the pointed tip 115 of the trocar 100 comes close to the bore of rim 44 (FIG. 10). Trocar 100 is then removed from the patient's body and instrument 10. Guide sleeve 33 is removed from guide bore 31 of guide ring 30. As shown in FIG. 11, this results in a small portal 310 in the patient's skin 300 and a small path 320 in the soft tissue 315 between the small portal 310 and bore 47 of rim 44.

Figure 12:
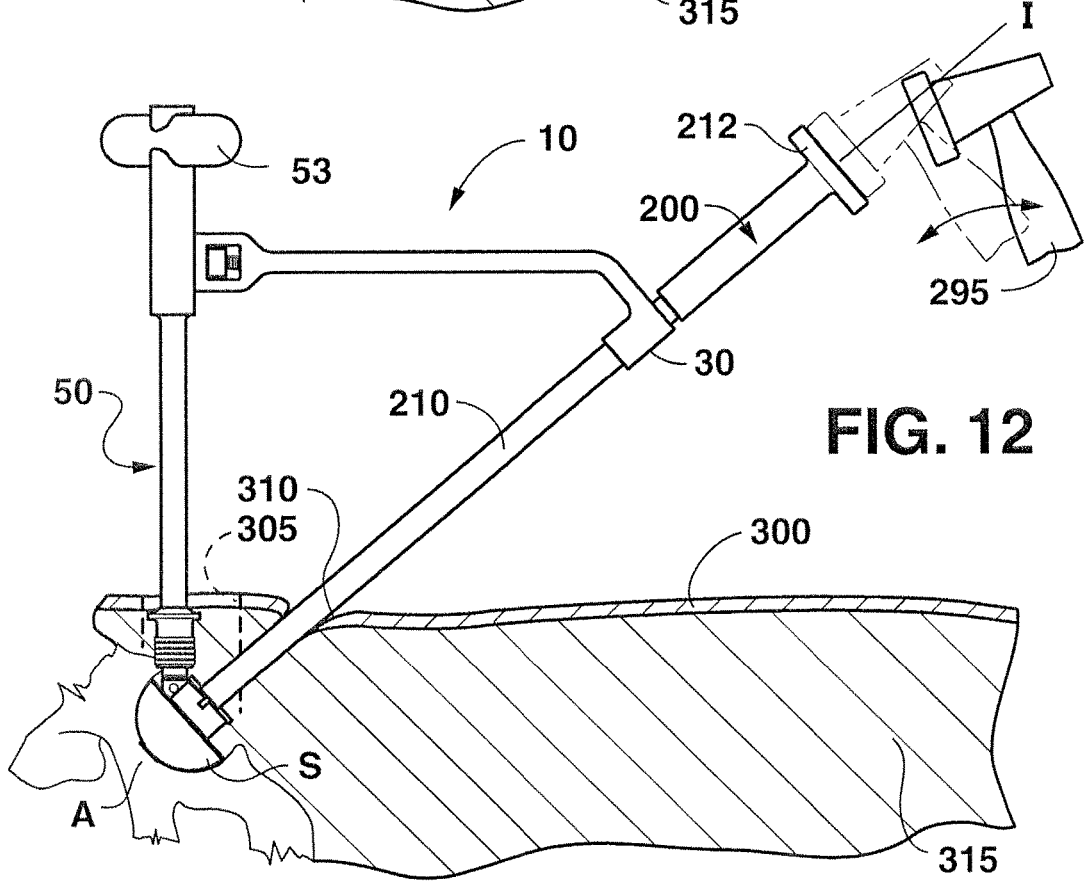

As shown in FIG. 12, impacting instrument 200 is then inserted through guide bore 31 of guide ring 30 and then further manipulated by the doctor through portal 310 and path 320 until keyed tip 211 is received within keyed bore 47 of rim 44. The doctor may then impart blows on the impacting end of impacting instrument 200 using, for example, a hammer 295. While impacting the blows of hammer 295, the doctor will continue to hold instrument 10 by handle 53 to make sure the blows continue to be imparted along the proper impaction axis I.

Figure 13:
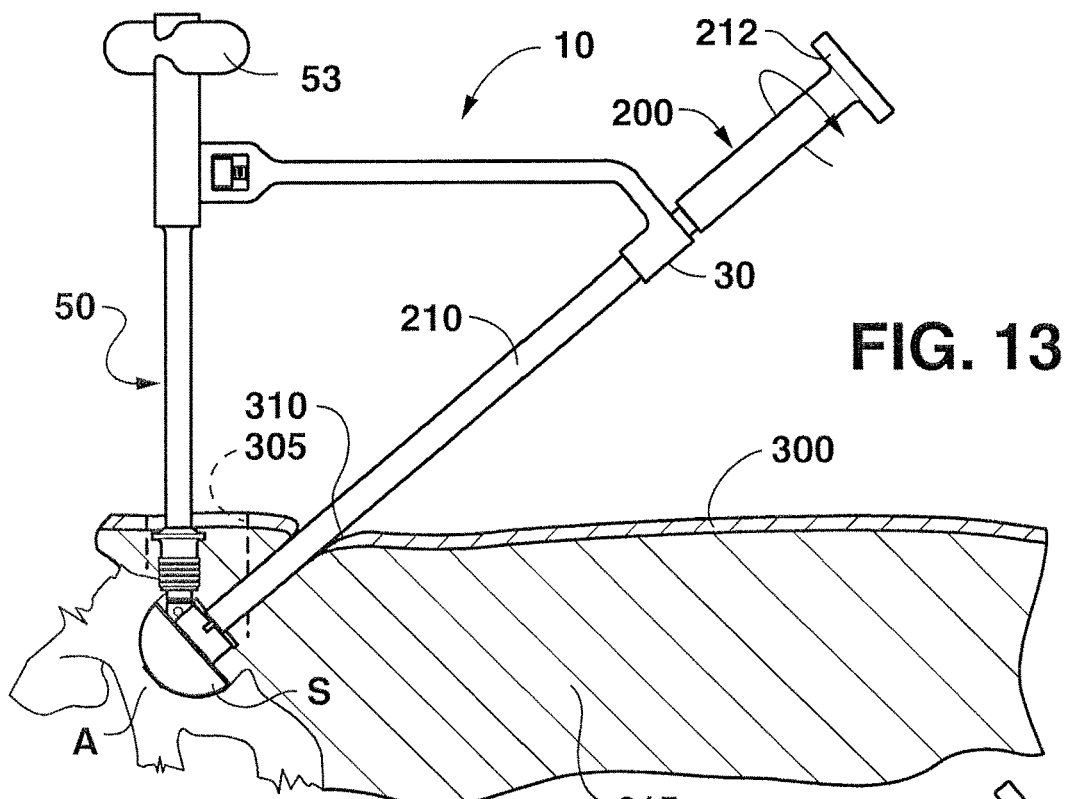
Figure 14:
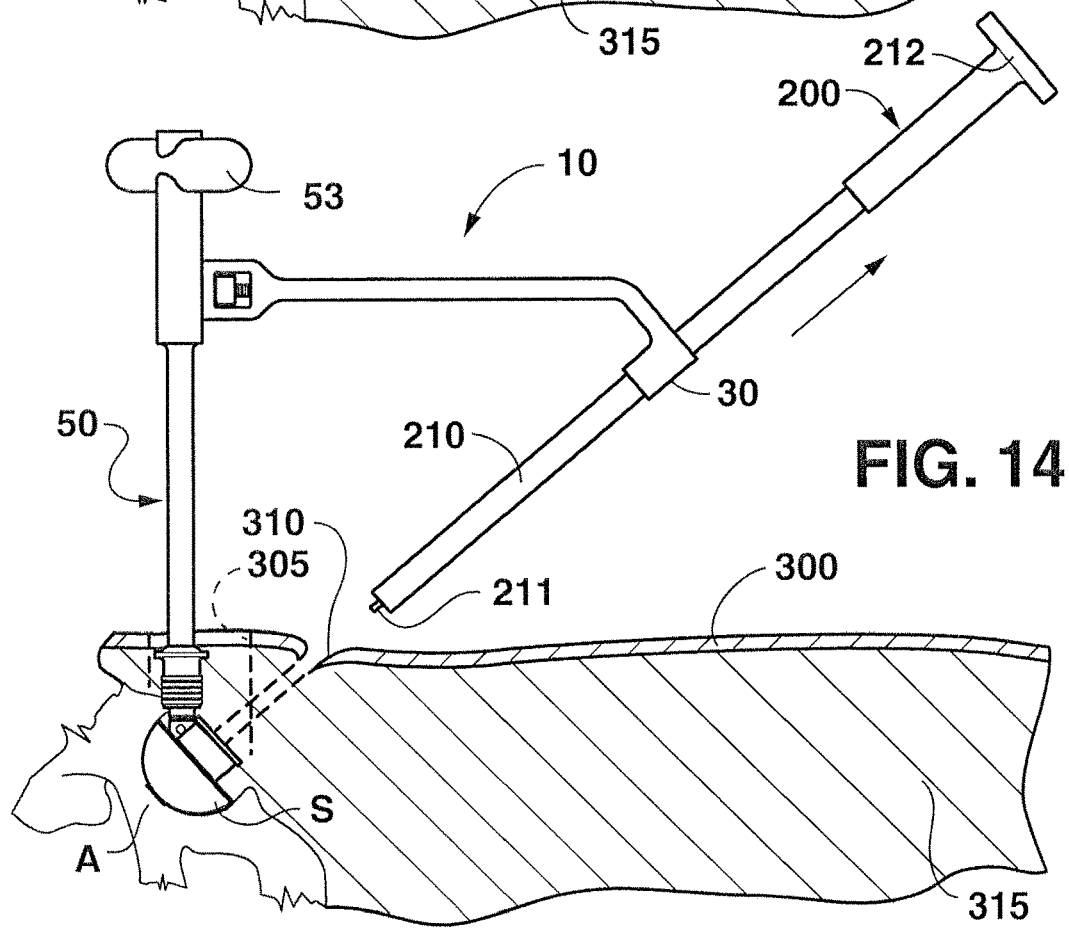

After the doctor is sure that the acetabular shell S is properly and firmly impacted within the patient's acetabulum A and the screws added if needed, as shown in FIG. 13, the doctor will rotate the handle 212 of impacting instrument 200. This will result in the rotation of rim 44, second impaction body portion 42, and threaded stud 41. The rotation of threaded stud 41 will ultimately result in the separation of acetabular shell S from threaded stud 41 and therefore instrument 10 (not shown due to scale). Finally, as shown in FIG. 14, impacting instrument 200 is removed from the patient's body and the guide bore 31 of guide ring 30. Instrument 10 is then removed from main incision 305 and the rest of the hip arthroplasty completed.

Figure 15A:
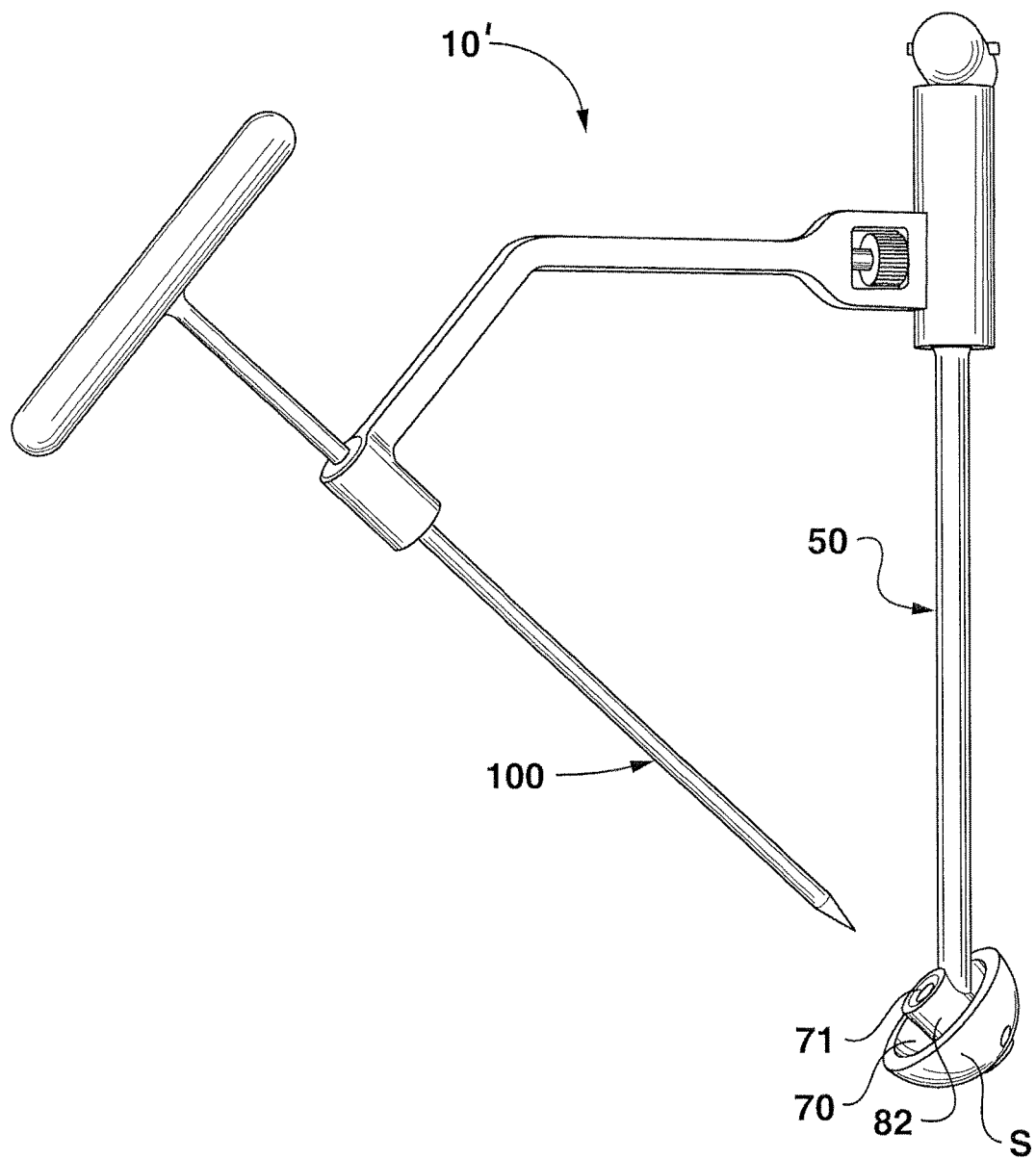
FIGS. 15A and 15B are second exemplary embodiments of the instrument according to the invention.
Figure 15B:
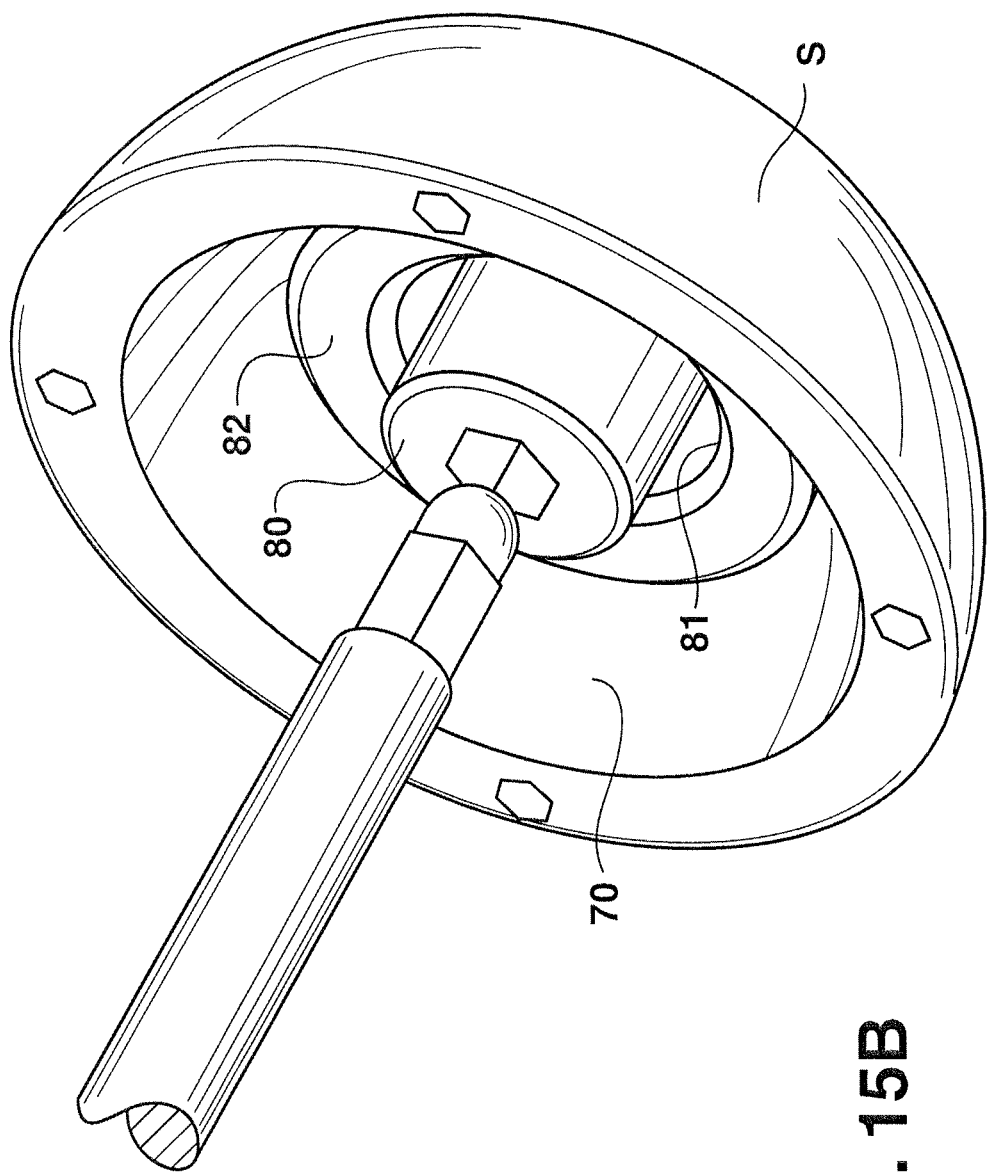

FIGS. 15A and 15B are second exemplary embodiments of the instrument according to the invention. Generally second exemplary embodiment is similar to the first embodiment. However, instrument 10' is different from instrument 10 in how acetabular shell S connects to instrument 10. In particular, impaction body 40 is simplified and streamlined into an angled sleeve member 70 having a bore 71 coaxial with the insertion axis I. A stud 80 having a threaded end (not shown) is passed through a gasket 82 made of a material that will not damage the inner surfaces of the acetabular shell S and screwed into bore 7, as previously described. Impaction body 70 is slipped over stud 80. Then, keyed tip 211 of impacting instrument 200 is mated with keyed bore 81 of stud 80 and instrument 10 operated as previously described. This simplified design is especially suitable for MIS methods.

Although this invention has been disclosed and illustrated with reference to particular exemplary embodiments, the principles involved are susceptible for use in numerous other embodiments which will be apparent to persons of ordinary skill in the art. The invention is, therefore, to be limited only as indicated by the scope of the appended claims.

What is claimed is:
1. A method of providing a minimally invasive hip arthroplasty in conjunction with a main incision formed through a patient's skin and soft tissue in said patient's hip, said main incision providing primary access to an acetabulum of said patient, comprising:
  providing an instrument, the instrument including a main body,
    the main body including a lengthwise portion extending to a lower end of the main body,
    an angled sleeve member formed on said lower end of said main body, said angled sleeve member having a sleeve bore therethrough,
    an arm, the arm having a straight first arm portion, the first arm portion extending from the main body below the handle, and a straight second portion extending from the first arm portion, the second portion angled downwardly relative to the first arm portion,
    a guide ring formed on an end of the second arm portion, the guide ring having a guide bore therethrough, and the guide bore axially aligned with the sleeve bore of the angled sleeve member to thereby form an impaction axis aligned with the guide bore and the sleeve bore,
  inserting the angled sleeve member through said main incision and into said acetabulum,
  providing a trocar, and, while said angled sleeve member is in said acetabulum, inserting the trocar through the guide bore until a tip of the trocar approaches said patient's skin,
  pushing the trocar through said skin and said soft tissue of said patient until the tip of the trocar comes into proximity with the angled sleeve in said acetabulum, and
  withdrawing the trocar from the instrument, thereby leaving a small portal incision in said patient's skin and a small path in said soft tissue between said small portal and said acetabulum.

2. The method of claim 1, further comprising providing a guide sleeve for the guide bore of the guide ring, said guide sleeve having an internal bore therethrough for receiving the trocar, and inserting the guide sleeve in the guide bore prior to the step of inserting the trocar in the guide bore.

3. The method of claim 2, wherein an outer diameter of said guide sleeve closely matches said guide bore of the guide ring, and a diameter of said internal bore of said guide sleeve closely matches an outer diameter of the trocar.

4. The method of claim 2, further comprising removing said guide sleeve from said guide ring after forming the small path with the trocar.

5. The method of claim 1, further comprising mounting an acebular component on the angled sleeve member prior to the step of inserting the angled sleeve member through said main incision and into said acetabulum, and using the acetabular component to orient the guide bore relative to said acetabulum.

6. The method of claim 5, further comprising providing an impacting instrument, inserting the impacting instrument through the guide bore of the guide ring, the small portal incision, and the small path until the impacting instrument is in position for impacting the acetabular component.

7. The method of claim 6, further comprising impacting the impacting instrument with an impactor.

8. The method of claim 7, further comprising, during the step of impacting, holding the instrument to make sure the blows continue to be imparted along the impaction axis.

9. The method of claim 1, wherein the lengthwise portion of the main body is straight.

10. The method of claim 1, further comprising a handle on an opposite upper end of the main body.

11. The method of claim 1, wherein the first arm portion of the arm extends perpendicularly from the main body.

* * * * *